(12) United States Patent
Tyberg et al.

(10) Patent No.: US 6,270,726 B1
(45) Date of Patent: Aug. 7, 2001

(54) TUBE BOTTOM SENSING FOR SMALL FLUID SAMPLES

(75) Inventors: William Tyberg, Spring Valley, NY (US); Arthur L. Babson, Chester, NJ (US)

(73) Assignee: DPC Cirrus, Inc., Randolph, NJ (US)

( * ) Notice: Subject to any disclaimer, the term of this patent is extended or adjusted under 35 U.S.C. 154(b) by 0 days.

(21) Appl. No.: 09/409,282

(22) Filed: Sep. 30, 1999

(51) Int. Cl.[7] .............................. G01N 21/00; G01N 1/10; G01N 35/10; B01L 3/02; G01F 23/00
(52) U.S. Cl. ..................... 422/100; 422/67; 73/864.24; 73/304; 73/149; 436/180
(58) Field of Search ................ 422/100, 67, 63; 436/180; 73/864.24, 864.23, 864.25, 304 C, 149

(56) References Cited

U.S. PATENT DOCUMENTS

| | | |
|---|---|---|
| 4,326,851 * | 4/1982 | Bello et al. ................. 23/230 R |
| 4,448,752 | 5/1984 | Banno et al. . |
| 4,622,208 | 11/1986 | Namba et al. . |
| 4,707,337 | 11/1987 | Jeffs et al. . |
| 4,721,680 | 1/1988 | Jeffs et al. . |
| 4,794,085 * | 12/1988 | Jessop et al. ................. 436/54 |
| 4,944,922 * | 7/1990 | Hayashi ......................... 422/100 |
| 5,045,286 * | 9/1991 | Kitajima et al. .............. 422/100 |
| 5,084,241 | 1/1992 | Parker . |
| 5,143,849 * | 9/1992 | Barry et al. ................... 436/50 |
| 5,223,225 | 6/1993 | Gautsch . |
| 5,270,210 | 12/1993 | Weyrauch et al. . |
| 5,304,347 | 4/1994 | Mann et al. . |
| 5,481,900 | 1/1996 | Husar . |
| 5,496,523 | 3/1996 | Gazit et al. . |
| 5,529,754 | 6/1996 | Bonacina et al. . |
| 5,550,059 | 8/1996 | Boger et al. . |
| 5,582,798 | 12/1996 | Meltzer . |
| 5,591,568 | 1/1997 | Bagchi et al. . |
| 5,665,601 * | 9/1997 | Kilmer ............................ 436/54 |
| 5,744,099 | 4/1998 | Chase et al. . |
| 5,753,514 | 5/1998 | Karlsson et al. . |
| 5,763,278 | 6/1998 | Sickinger et al. . |
| 5,820,824 | 10/1998 | Tanaka . |
| 5,843,378 * | 12/1998 | El-Hage et al. ............... 422/180 |
| 5,855,851 | 1/1999 | Matsubara et al. . |
| 5,895,630 * | 4/1999 | Skaborn et al. ............... 422/100 |

* cited by examiner

Primary Examiner—Jill Warden
Assistant Examiner—B R Gordon
(74) Attorney, Agent, or Firm—McGuireWoods LLP

(57) ABSTRACT

A pipetting station having a bottom sensing device is provided in conjunction with one of any known liquid level sensing devices. The bottom sensing device includes a pipetting probe spring mounted to a pipetting arm of the pipetting station. The bottom sensing device also includes a sensor for determining when a pipetting tip of the pipetting probe is in contact with a bottom of a tube. The bottom sensing device permits the pipetting probe to measure an exact volume of fluid in the tube by allowing the pipetting tip to be lowered to the bottom of the tube beyond the sensed fluid level.

12 Claims, 7 Drawing Sheets

TUBE BOTTOM SENSING FOR SMALL FLUID SAMPLES

BACKGROUND OF THE INVENTION

1. Field of the Invention

The present invention generally relates to a method and apparatus for sensing small fluid samples in a vessel and, more particularly, to a method and apparatus for determining the volume of a fluid in a vessel, such as a test tube, using a bottom sensing device (e.g., tip jam device).

2. Background Description

Analyses of fluids, especially bodily fluids such as urine and blood, are important to the diagnoses and treatment of various illness and other conditions. These illnesses and conditions can range from various forms of cancers to blood diseases to drug use and others.

In order to analyze a bodily fluid, a sample of fluid is first taken from a person and analyzed either by hand or by an automatic analyzer or other device of the type well known in the art. In the case of an automatic analyzer, for example, the bodily fluid is disposed in a tube which, in turn, is disposed on a carousel or other conveying mechanism. The carousel or other conveying mechanism conveys the tube though scanning stations, for example, and under a pipetting station in order for a pipetting probe to aspirate a sample of the fluid.

The pipetting probe is then lowered into the tube in order to aspirate a sample of the fluid. Thereafter, and depending on the specific test or tests to be performed on the fluid, a specific reagent may be combined with the fluid in order for a chemical reaction to occur. This chemical reaction is then analyzed to determine, for example, the amount of analyte in a sample of fluid.

It is not uncommon for many different tests to be performed on the sample fluid using different reagents. However, in order for the appropriate tests to be performed on the sample fluid a sufficient amount of the sample fluid must be present in the tube. Accordingly, when using automatic analyzers, the sample level in the tube is normally determined by the pipette probe which is connected to a sample sensing means such as a capacitive or conductive circuit. The sensing means is triggered upon contact of the pipette tip with the surface of the sample. The pipette probe is then further lowered a distance into the sample sufficient to allow withdrawal of the required volume. However, to ensure that an insufficient volume of sample will not be drawn, owing to the sample level being too close to the bottom of the tube, the pipette tip will only be allowed to be lowered to a certain level within the tube resulting in a volume of sample, called the dead volume, that is unavailable for testing. The maximal distance the pipette tip is allowed to be lowered, and thus the nominal dead volume, is set by the manufacturer of the automatic analyzer It is noted that the actual dead volume is variable and is dependent on several dimensional tolerances that exist within and between different instruments. A more dimensionally precise automatic analyzer would allow the pipette tip to aspirate fluids at a lower level than other less precise automatic analyzers, and thereby allow the manufacturer to set a smaller sample dead volume. Any amount of sample fluid below the preset dead volume level can not be utilized to perform a test or tests thereon despite the fact that the fluid in the test tube below the dead volume level may still be sufficient to perform a test or tests thereon.

Thus, what is needed is a system that determines the exact volume of a fluid below a threshold level which may be defined as a near bottom tube level. It is noted that the near bottom tube level is an arbitrary level of fluid in the tube, and may be predefined by the manufacturer of an automatic analyzer. The determination of the exact volume of a fluid in the tube will allow the automatic analyzer or other device to determine whether there is a sufficient amount of fluid in the tube in order to perform a certain predetermined test or tests.

SUMMARY OF THE INVENTION

It is therefore an object of the present invention to provide a system and method for determining a bottom of a tube or other container.

It is a further object of the present invention to provide a system and method for determining the volume of a fluid in a tube or other container.

It is also an object of the present invention to provide a system and method of measuring a reagent in a reagent container.

It is still another object of the present invention to provide a system and method for determining whether a sufficient amount of fluid is present in a tube for a specific test or tests.

In order to accomplish the objects of the present invention, a pipetting station having a bottom sensing device is provided in conjunction with one of any known liquid level sensing devices. The bottom sensing device includes a pipetting probe spring mounted to a pipetting arm of the pipetting station. The bottom sensing device also includes a sensor for determining when a pipetting tip of the pipetting probe is in contact with a bottom of a tube.

The bottom sensing device of the present invention permits the pipetting probe to measure the volume of fluid in the tube by allowing the pipetting tip to be lowered to the bottom of the tube beyond the sensed fluid level (and the near bottom tube level). In the embodiments of the present invention, the pipetting arm is further lowered until the pipetting probe triggers a sensor which stops the downward movement of the pipetting arm. The exact distance between actual tip jam and triggering of the tip jam sensor, and therefore the actual bottom of the tube, is known and configured for each instrument.

A determination is then made as to (i) an exact volume of fluid and (ii) whether there is sufficient sample fluid in the tube to perform a test or tests thereon. The determination of the volume of fluid in the tube is based on (i) the sensed level of the fluid as determined by the level sensor (in relation to a "home" position of the pipetting arm), (ii) the distance the pipetting arm traveled from the level of the sample fluid to the time when the pipette tip contacts the bottom of the tube and (iii) the type of tube used for holding the fluid. If sufficient fluid is present, then the pipetting tip is raised slightly above the known tube bottom level in order to aspirate sample fluid or reagent therefrom.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

The present invention is directed to a method and apparatus for sensing fluids of small samples in a tube and, more specifically, to a method and apparatus for determining the volume of a fluid in a tube that is below a near bottom tube level using a bottom sensing device. The bottom sensing device is used to determine the volume of a fluid in a tube, as described in detail below. By using the apparatus and method of the present invention, a pipetting station of an automatic analyzer or other device may aspirate fluids of small samples for testing thereon.

In order to accomplish the objectives of the present invention, a bottom sensing device is implemented in conjunction with a pipetting tip having a capacitive level sensor or other means of sensing fluid levels. A pipetting capacitive level sensor contemplated for use with the present invention is disclosed in U.S. Pat. No. 5,648,727 and is incorporated herein by reference in its entirety. In general, the capacitive level sensor disclosed in U.S. Pat. No. 5,648,727 includes a pipetting probe having an elongated shaft having a conductive tip, and an integrated circuit chip containing a capacitive sensing circuitry. When the conductive tip is lowered and contacts a sample fluid, an increase in capacitance is sensed. This sensed increase in capacitance is used to determine the level of the sample fluid in relation to a "home" position of the pipetting arm. It is well understood that other level sensors may also be used with the present invention, such as, for example, electrically conductive sensors or air pressure sensors.

The bottom sensing device includes a spring loaded pipetting arm having a sensor which senses when the pipetting tip is in contact with the bottom of the tube. It is noted that the automatic analyzer or other device does not identify that the pipetting tip is in contact with the bottom of the tube until after the sensor is triggered. Accordingly, the automatic analyzer or other device identifies the bottom of the tube when the spring loaded pipetting arm travels until the sensor is "flagged" (e.g., triggered). The distance between the actual tube bottom and the triggering of the sensor is a known configured number of steps on a stepper motor. In a preferred embodiment, the triggering of the sensor will stop the downward movement of the pipetting arm.

Figure 3A:
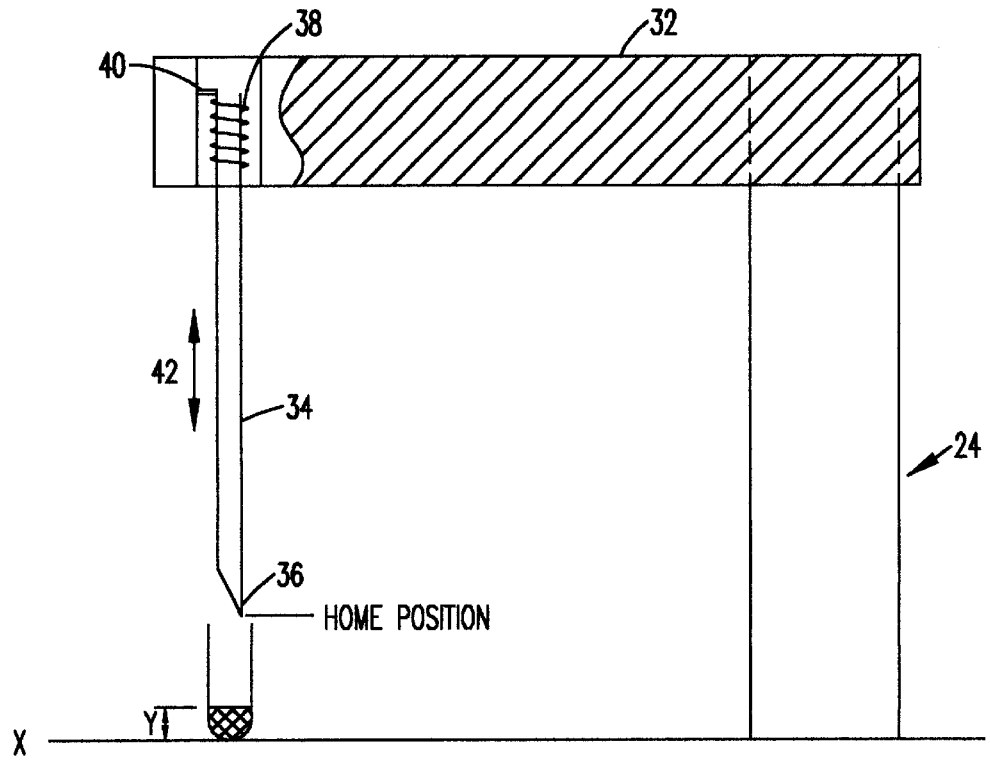
FIG. 3a is a pipetting station in a raised position using a bottom sensing device of the present invention.
Figure 3B:
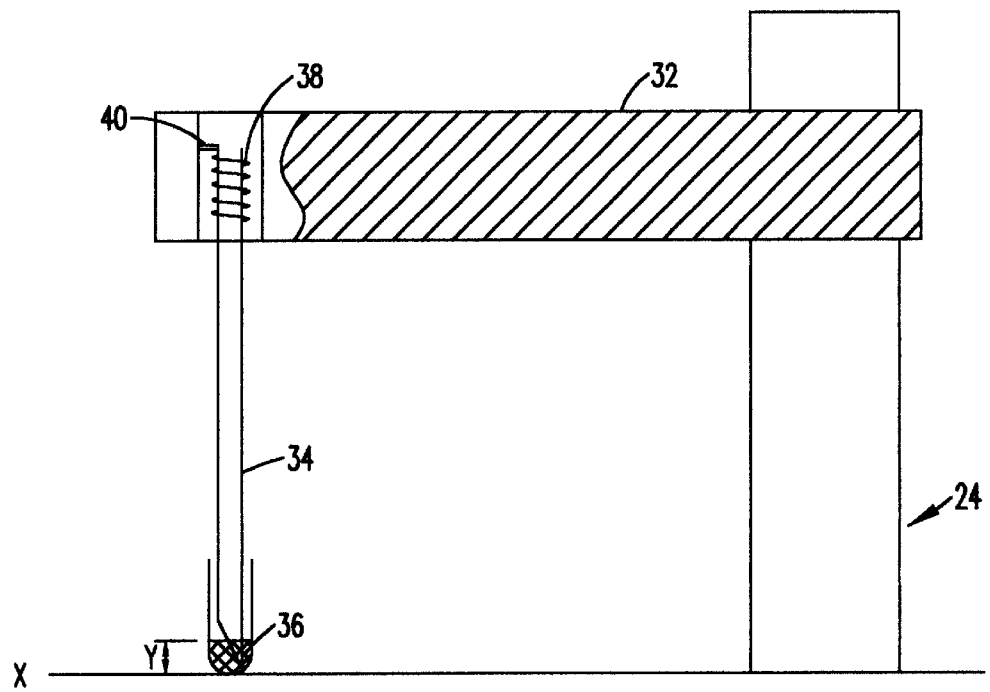
FIG. 3b is a pipetting station in a lowered position using a bottom sensing device of the present invention.
Figure 3C:
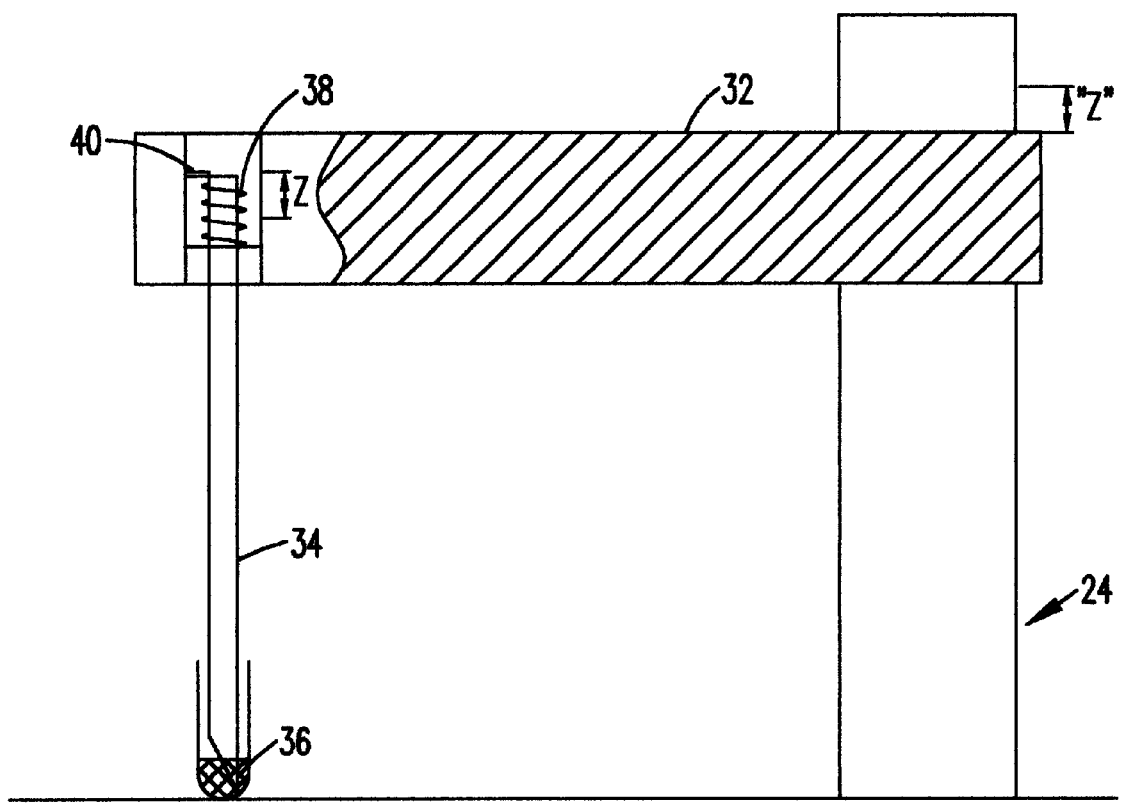
FIG. 3c is a pipetting station in a lowered position with the bottom sensing device of the present invention being activated.
Figure 5:
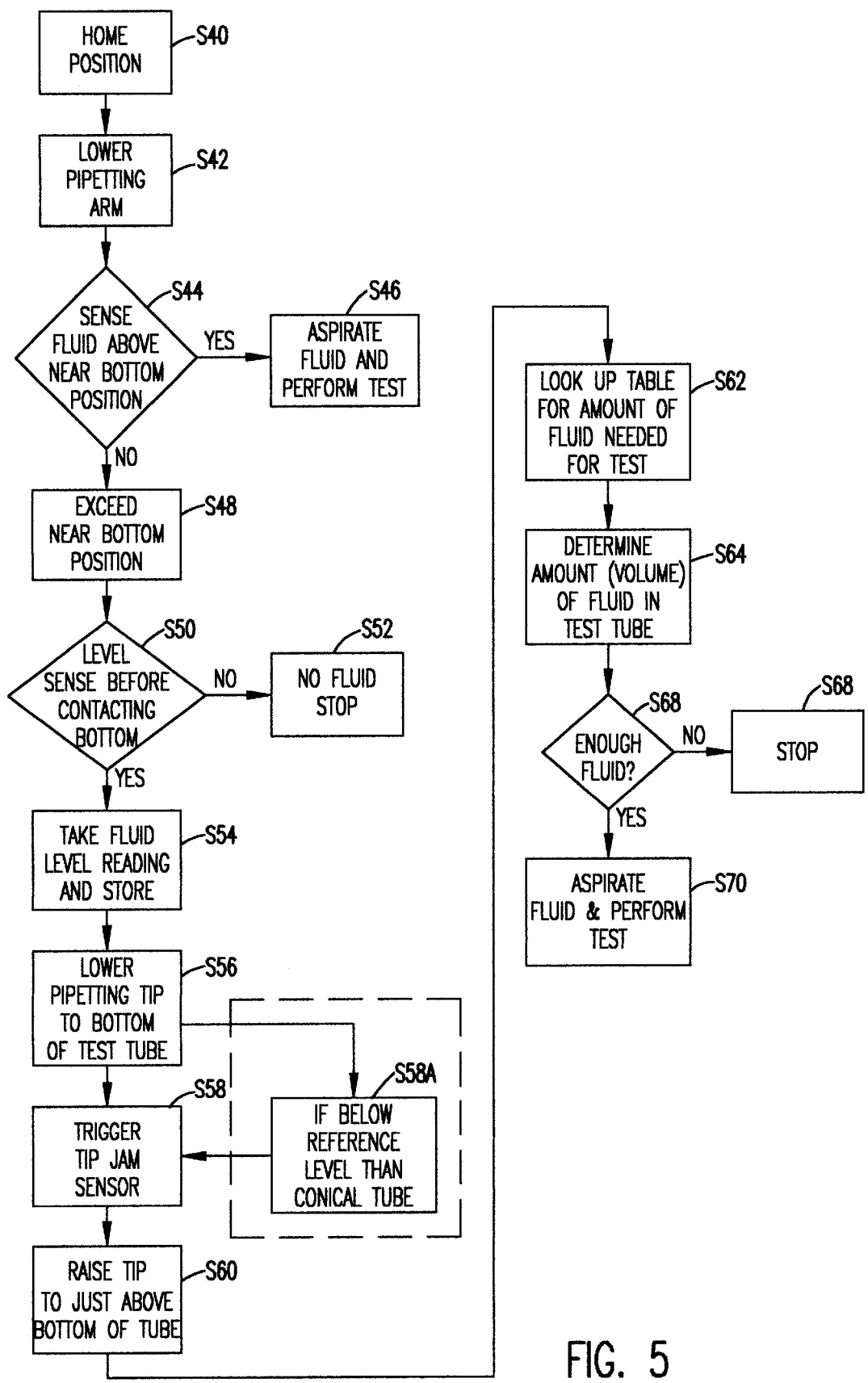
FIG. 5 is a flow chart of the processing steps of the present invention.
Figure 6:
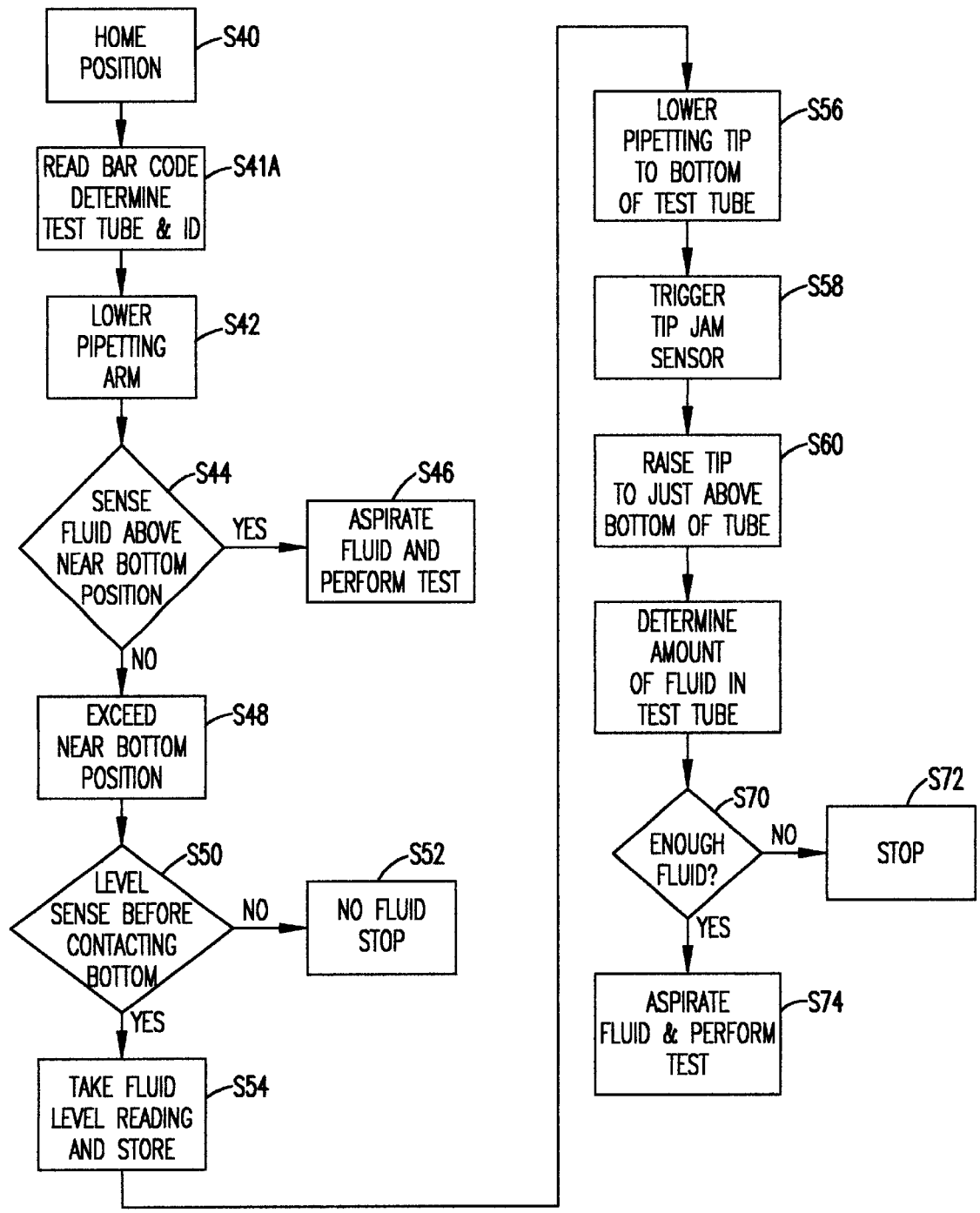
FIG. 6 is an alternate flow chart of the processing steps of the present invention.

In the preferred embodiments, once the pipetting arm is raised or during raising thereof, a determination may be made as to (i) the volume of fluid and (ii) whether there is sufficient sample fluid in the tube to perform a test or tests thereon. The determination of the volume of fluid in the tube is based on, in part, (i) the distance the pipetting arm traveled from the level of the sample fluid to the time when the sensor was triggered minus the certain distance traveled after the pipetting tip is in contact with the bottom of the tube and (ii) the known shape of the type of tube used to hold a sample fluid. FIGS. 3a–3c show a detailed view of the pipetting station using the bottom sensing device of the present invention, and FIGS. 5 and 6 show a detailed flow diagram explaining a process used with the bottom sensing device of the present invention.

Figure 1:
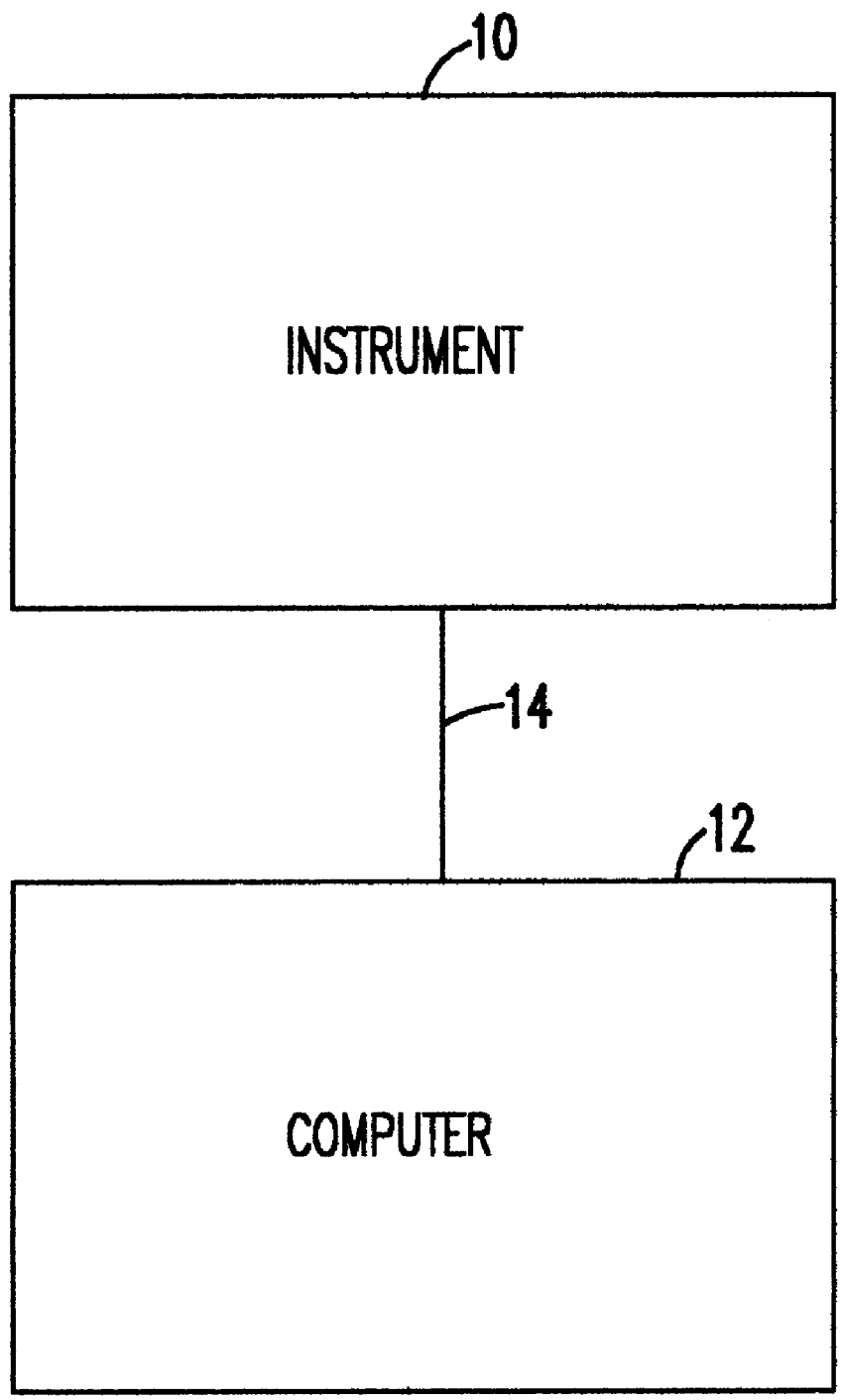
FIG. 1 is generalized block diagram of an instrument used with the present invention.

In order to practice the present invention, an automatic analyzer or other known device is needed to perform the specific tests on the fluid samples. In general, FIG. 1 shows a block diagram of an automatic analyzer which may be used with the present invention. The automatic analyzer 10 is connected to a computer 12 via data communication lines 14 which are used to supply information from the automatic analyzer 10 to the computer 12. This information may be, for example, bar coded information placed on the sample fluid tubes. The automatic analyzer 10 is preferably operated under the direction of onboard microprocessors (not shown). It is well understood that the block diagram of FIG. 1 is not critical to the understanding of the present invention and that other devices depicted in other block diagrams may equally be used with the present invention, including non-medical devices.

Figure 2:
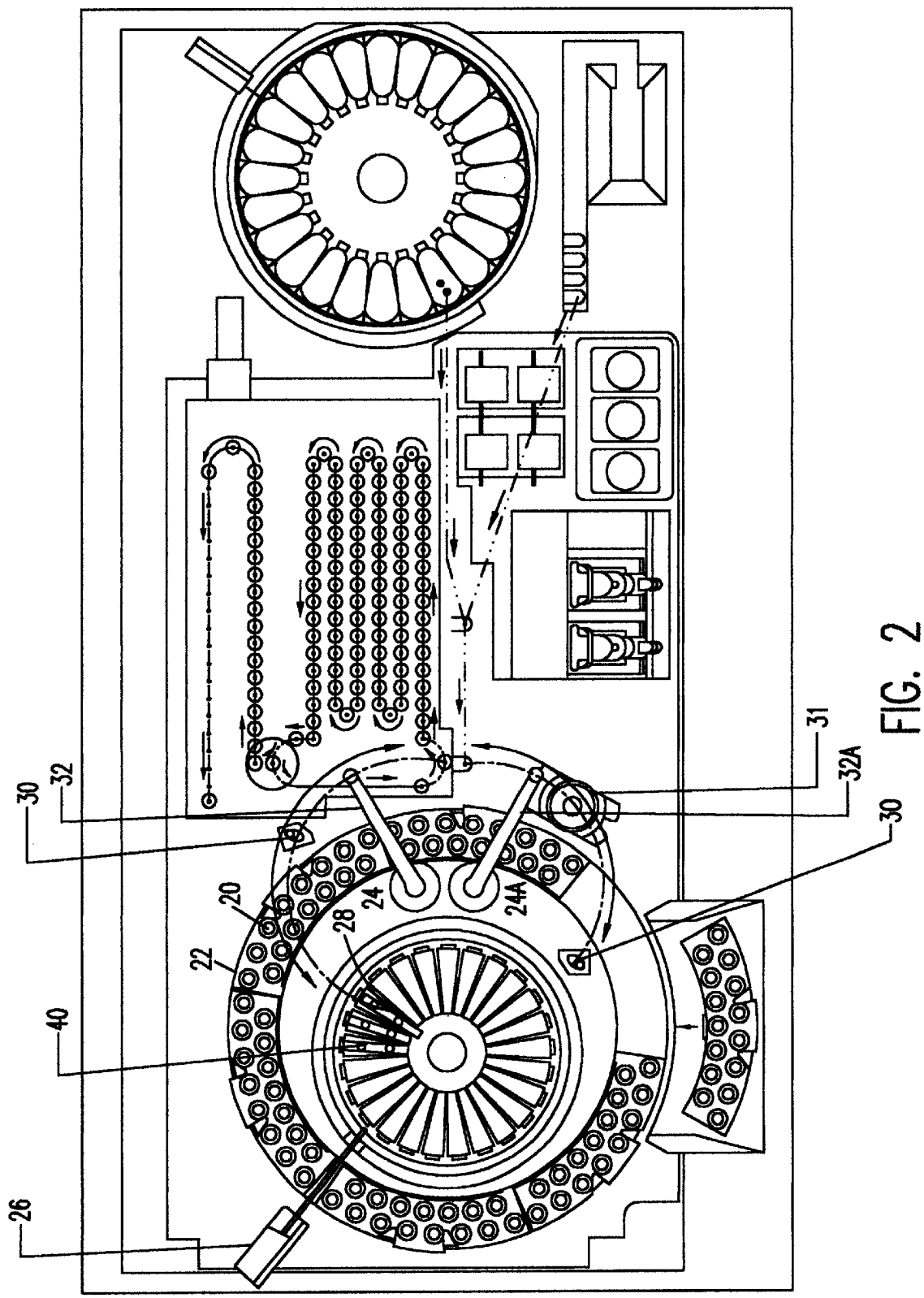
FIG. 2 is a partial view of an automated analyzer used with the present invention.

FIG. 2 shows a partial view of the automatic analyzer 10 in greater detail. It is noted that the automatic analyzer 10 of FIG. 2 is an IMMULITE 2000™ manufactured by DPC® Cirrus (a subsidiary of Diagnostic Products Corporation) of Randolph, New Jersey; however, it is noted that the automatic analyzer of FIG. 2 is merely representative of one automatic analyzer used with the present invention and it is well understood that the present invention may easily be implemented with other automatic analyzers or other fluid sample devices known to one of ordinary skill in the art. It is further important to note that the automatic analyzer of FIG. 2 is merely described herein for illustrative purposes and to better understand the present invention, and that only the bottom sensing device of the pipetting station and the method of use discussed herein (with reference to FIGS. 3a–6) are part of the present invention.

Referring more specifically now to FIG. 2, a sample carrier tube 20 is transported by a carousel 22 towards a reagent pipetting station 24 and sample pipetting station 24A. Prior to being transported to the pipetting stations 24 or 24A, the sample carrier tube 20 may be transported through a bar code reader 26. In the embodiments of the present invention, the bar code reader 26 may identify the person (of which the sample fluid belongs to) or type of tube being used such as, for example, a pediatrics or micro sample tube. In the case of a pediatrics or micro sample tube, the computer of FIG. 1 will include an alternative look-up table in order to calculate the volume of the fluid in the sample, as discussed below.

It is noted that the information from the bar code reader 26 is sent to the memory of the computer 12, which may also track the position of the sample carrier tube 20 on the carousel 22. It is further noted that the computer may be preprogrammed to include the volume table of known volumes of tubes (such as conical bottom tubes and micro sample tubes) as well as the volume of fluid needed to perform a certain test or tests on the fluid. The computer may also be programmed to prioritize which tests may be performed with the amount of fluid present in the tube. For example, if three tests must be performed on the fluid, the system and method of the present invention may prioritize that the first and third test be performed to the exclusion of the second test since only enough sample fluid is present in the tube to perform the first and third test. Of course other variations may also be provided for by the present invention.

As seen further in FIG. 2, the reagent pipetting station 24 and sample pipetting station 24A include a reagent pipetting arm 32 and a sample pipetting arm 32A, respectively, which both may travel a circular path. (Hereinafter, the reagent pipetting station 24 and sample pipetting station 24A are referred to as the pipetting station 24 and the reagent pipetting arm 32 and sample pipetting arm 32A are referred to as the pipetting arm 32.) In this path, the pipetting arm 32 may extend to the sample carrier tube 20 in the carousel 22, a reagent 28 in the reagent carousel 40, and a probe wash station 30. The pipetting arm 32 may also travel in other paths, and may equally extend to other carriers or stations, such as for example, a sample dilution well 31. A downward projecting pipetting tip (shown in FIGS. 3a–3c) is positioned at the free end of the pipetting arm 32. To perform pipetting operations, the pipetting tip is inserted into and out of the sample carrier tubes 20 and other stations along its Z-axis (perpendicular to the plane of the paper).

Referring now to FIG. 3a, a detailed view of the pipetting station in a "home" position is shown. The pipetting station 24 includes the pipetting arm 32 that moves in the direction of arrow 42, and a pipetting probe 34 spring mounted to the pipetting arm 32 of the pipetting station 24. The pipetting probe 34 includes a pipetting tip 36 having a capacitive level sensor as described with reference to U.S. Pat. No. 5,648,727. The capacitive sensor senses a level of the fluid and determines that level in relation to a known "home" position. The tube 20 is placed in a holding device (see FIG. 4) so that a bottom of the tube 20 is at the reference line "X" which is used as a reference point for discussion purposes only.

The bottom sensing device of the present invention includes a spring mechanism 38 and a sensor 40 mounted between the pipetting probe 34 and the pipetting arm 32. Specifically, the spring mechanism 38 is mounted to the pipetting probe 34 in the pipetting arm 32 and permits the pipetting arm 32 to work independently of the pipetting probe 34 as seen more clearly with reference to FIG. 3b and FIG. 3c. In general, the pipetting arm 32 lowers the pipetting probe 34 until the pipetting tip 36 is in contact with the bottom of the tube 20 (past a near bottom tube level) (FIG. 3b). The pipetting arm 32 is then further capable of being lowered an incremental distance while the pipetting probe 34 remains stationary and the pipetting tip 36 is in contact with the bottom of the tube 20 (FIG. 3c).

The sensor 40, preferably positioned proximate the pipetting arm 32, determines when the pipetting arm 32 has traveled the incremental distance, such as, for example, approximately in the range of 1 mm to 4 mm or more, while the pipetting probe 34 remains stationary (represented as "Z" distance in FIGS. 3b and 3c). It is noted that the bottom sensing device of the present invention determines that the pipetting tip 36 is in contact with the bottom of the tube 20 when the sensor 40 is triggered, at which time the downward movement of the pipetting arm 32 is stopped, and in embodiments the pipetting tip 36 may be raised an incremental amount within the fluid so that pipetting tip 36 will not become occluded when aspiration of the fluid begins.

FIG. 3b shows the pipetting probe 34 in a lowered position and the pipetting tip 36 in contact with the bottom of the tube 20. As seen with reference to the line "X", the tube 20 remains stationary throughout the process while the pipetting arm 32 and pipetting probe 34 are lowered. It is readily apparent that the pipetting arm 32 and the pipetting probe 34 are synchronously lowered until the pipetting tip 36 is in contact with the bottom of the tube 20.

FIG. 3c shows the pipetting arm 32 being lowered an incremental distance "Z" while the pipetting probe 34 is stationary and the pipetting tip 36 is in contact with the bottom of the tube. At this stage the sensor 40 is activated after the pipetting arm has been lowered the incremental distance "Z". The independent movement of the pipetting arm 32 with relation to the pipetting probe 34 is due to the spring loaded mechanism 38 described with reference to FIG. 3a. It is noted that the incremental distance between the actual bottom of the tube and the triggering of the sensor of the pipetting arm 32 is configured for each individual pipetting station 24 such that the traveled distance may vary between different pipetting stations.

Thus, by using the bottom sensing device of the present invention, the pipetting tip 36 can be lowered past the level of the fluid and the volume measurement of the fluid in the tube 20 can be determined. This is provided by the use of the spring loaded mechanism 38 in conjunction with the independent movement of the pipetting arm 32 and the activation of the sensor 40 as discussed with reference to FIGS. 3a–3c. Once the volume of fluid is known, the system of the present invention can determine whether a sufficient amount of fluid remains in the tube 20 in order to perform a certain predefined test. The volume of the sample fluid in the tube 20 is calculated by (i) a known volume based on a type of tube used to hold a sample fluid, (ii) a top level of the sample fluid in the tube as sensed by the level sensor, and (iii) a distance of movement of the pipetting arm minus the certain distance the pipetting arm traveled after the pipetting tip is in contact with the bottom of the tube. Alternatively, the present invention can prioritize between which tests are to be performed on the fluid, as discussed above.

Figure 4:
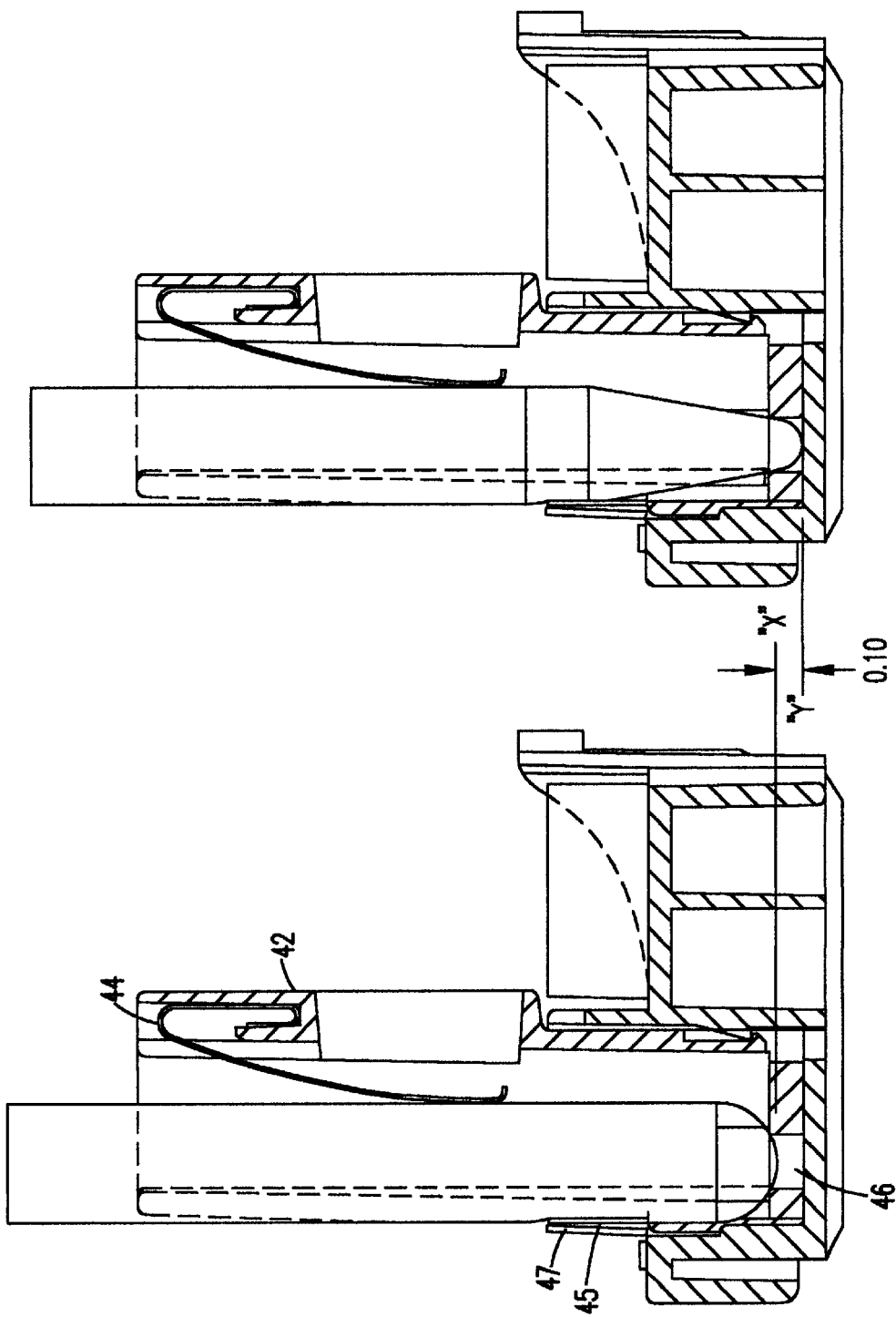
FIG. 4 is a comparison of a standard tube and a conical bottom tube located in a tube holding device.

FIG. 4 shows a comparison between a standard tube (having a rounded bottom) and a conical bottom tube in a tube holding device. Specifically, the standard tube is held in the tube holding device 42 by use of a resilient spring 44 biasing the standard tube against a wall 47 of an opining 45. At a bottom of the tube holding device 42 is an opening 46. The opening 46 is configured such that the bottom of the standard test tube remains at the reference line "X" as discussed with reference to FIGS. 3a–3c. However, the opening 46 allows the bottom of the conical shape tube to exceed beyond the reference line "X" to reference line "Y". In the preferred embodiment, the distance between the reference line "X" and the reference line "Y" is about 0.10 inches; however, it is well understood that any other distance may also be contemplated for use with the present invention. As discussed in more detail with reference to FIGS. 5 and 6, the pipetting tip may be lowered past the reference line "X" (step S58a) to reference line "Y" such that the system of the present invention will automatically identify that a conical shaped bottom tube is being used with the present invention. In this case, when the system of the present invention automatically identifies that such a conical shaped bottom tube is being used, the sample volume of the tube will be calculated by reference to an alterative look-up table which is different from the look-up table for the standard tube.

Prior to discussing FIGS. 5 and 6, it is noted that the calculation of the volume of the fluid in the tube is calculated by the CPU of the computer or other similar device. It is also readily understood by one of ordinary skill in the art that all other calculations and determinations discussed herein are also calculated by the CPU of the computer or other similar device. These calculations and determinations may further include the prioritization of the tests being performed on the fluid as well as the near tube bottom position (e.g., the position of prior art systems in which one was assured that there was enough fluid to run a specific test or tests).

More specifically, the invention can be implemented using a plurality of separate dedicated or programmable integrated or other electronic circuits or devices (e.g., hard-wired electronic or logic circuits such as discrete element circuits, or programmable logic devices such as PLDs, PLAs, PALs, or the like). A suitably programmed general purpose computer, e.g., a microprocessor, microcontroller or other processor device (CPU or MPU), either alone or in conjunction with one or more peripheral (e.g., integrated circuit) data and signal processing devices can be used to implement the invention. In general, any device or assembly of devices on which a finite state machine capable of implementing the flow charts shown in FIGS. 5 and 6 can be used as a controller with the invention.

FIG. 5 is a flow diagram showing the process of using the bottom sensing device of the present invention. Specifically, at step S40, a "home position" is determined and stored in the memory of the computer. At step S42, the pipetting arm is lowered and, at step S44, a determination is made as to whether any fluid is sensed at or above a near tube bottom level position, typically 250 μl or other determined level. If fluid is sensed at the near bottom tube level position, at step S46, a sample of the fluid is aspirated into the pipetting probe and a test is performed thereon. However, if no fluid is sensed at the near bottom tube level position, at step 48, the pipetting arm is lowered until a fluid level is sensed. At this step, it is preferred that the lowering of the pipetting arm be slower than the previous movement of the pipetting arm to ensure that the pipetting tip does not contact the bottom of the tube at such a rate of speed as to damage or destroy the tube or pipetting tip or arm.

At step S50, a determination is made as to whether the pipetting tip is in contact with the bottom (discussed in detail below) of the tube fluid prior to sensing any fluid within the tube. If no fluid is sensed, a determination is made that there is no fluid in the tube and the process of the present invention stops, at step S52. However, if a fluid is sensed, at step S54, a position reading of the pipetting arm (or probe or tip) with relation to a "home" position is determined and stored in the memory of the computer. The position reading is determinative of the level of sensed fluid.

At step S56, the pipetting tip is lowered until it is in contact with the bottom of the tube. As discussed above, the pipetting station does not know that the pipetting tip is in contact with the bottom of the tube at this step. Thus, in order to determine that the pipetting tip is in contact with the tube, at step S58, the pipetting arm is lowered an incremental distance while the pipetting probe remains stationary until the sensor is triggered. Once the sensor is triggered at step S58, the downward movement of the pipetting arm is stopped. At step S60, the pipetting arm and pipetting probe may be raised an incremental amount within the fluid, preferably just above the known tube bottom level, so that the pipetting tip 36 will not become occluded when the fluid is aspirated by the pipetting probe. It is at this step S58, that the pipetting station knows that the pipetting tip is in contact with the bottom of the tube and may thus determine the volume of fluid present in the tube.

In an alternate embodiment, the pipetting tip may be lowered past the reference line "X" (step S58a) by a certain distance such that the system of the present invention will identify that a conical shaped bottom tube is being used with the present invention. This is based on the fact that the conical shaped tube, in the embodiments of the present invention, preferably extend past the reference line "X" so that when the pipetting tip passes the reference line "X" the system of the present invention will automatically identify that such a conical shaped bottom tube is being used herein. In this case, the sample volume will be calculated by reference to an alterative look-up table which is different from the look-up table for a standard tube.

At step S62, the volume of fluid in the tube is determined (as described above with reference to FIG. 3a). That is, the volume of the tube is calculated by using a look-up table for the tube and by(i) a known shape of the type of tube used to hold a sample fluid, (ii) a top level of the sample fluid in the tube as sensed by the liquid level sensor, and (iii) a distance of movement of the pipetting arm minus the certain distance the pipetting arm traveled after the pipetting tip is in contact with the bottom of the tube.

At step S66, a determination is made as to whether there is sufficient amount of fluid in the tube to perform desired specific tests. If there is not a sufficient amount of fluid, then the process of the present ends at step S68. However, if there is enough fluid present in the tube, then at step S70, the present system may prioritize which tests may be performed on the fluid sample and being aspiration of the fluid for testing thereon. Alternatively, the operator can be alerted that insufficient sample is available to complete all of the required tests, and the operator can then select manually which test or tests may be performed on the sample fluid.

As discussed above, a known volume table for tubes is provided to the system of the present invention. This allows the present invention to "look up" an appropriate table in order to calculate the volume of the tube based on the movement of the pipetting arm with relation to a sensed level of the fluid and a determined bottom position of the tube. It is also readily understood by one of ordinary skill in the art that the system of the present invention also stores in memory or the like the amount of fluid needed for the specific test or tests.

FIG. 6 is a flow diagram showing an alternative process of using the bottom sensing device of the present invention. In this embodiment, the sample tube is a conical or a round bottom micro tube which is contained in a special bar coded insert or rack. In the case of the micro tube (and in embodiments the conical bottom tube), an identification is provided by a second interrogation of the sample carousel or conveyer by the bar code reading station. The preconfigured new tube bottom position based on the detected tubes would be different from each of these tubes as well as being different from the standard tube. It is further noted that each tube has its own look-up table such that the sample volume of each different tube may be calculated by reference to a specific look-up table.

More specifically, after step S40, the tube is passed by a bar code scanner for reading of a bar code (step S41a). This step may also be performed prior to step S40. The bar code reader provides the bar code information to the computer such as, but not limited to, (i) the type of tube being used to hold the fluid and (iii) the identifying information of the fluid (e.g., person). In this embodiment of the present invention, the system of the present invention may also consult a look up table to determine the amount of fluid needed for a specific test or tests to be performed on the fluid. The remaining steps of FIG. 5 may then be implemented.

It is noted that when using the conical bottom tube, the system of the present invention will automatically identify such a conical bottom tube when the pipetting tip exceeds the reference line "X" at step S56.

While the invention has been described in terms of a single preferred embodiment, those skilled in the art will recognize that the invention can be practiced with modification within the spirit and scope of the appended claims.

Having thus described our invention, what we claim as new and desire to secure by letters patent is as follows:

1. A bottom sensing device for determining a bottom of a container, comprising:

mounting means for mounting a pipetting probe on a pipetting arm, the mounting means allowing the pipetting arm to move a predetermined incremental distance independent of the pipetting probe when the pipetting tip contacts a bottom of the container; and sensing means for sensing when the pipetting tip is in contact with the bottom of the container, the sensing means being activated when the predetermined pipetting arm moves the incremental distance.

2. The bottom sensing device of claim 1, wherein the container is one of a test tube and a reagent container.

3. The bottom sensing device of claim 1, further comprising calculating means for calculating a volume of the fluid in the container, the volume being calculated based on (i) a known shape of a type of container used to hold a sample fluid, (ii) a top level of the sample fluid in the container as sensed by a sensing means, and (iii) a distance of movement of the pipetting arm from the top level of the sample fluid to when the pipetting tip is in contact with the bottom of the container.

4. The bottom sensing device of claim 3, wherein the calculating means further calculates a distance from the top level of the fluid to the bottom of the container by subtracting the incremental distance of the pipetting arm from an entire distance of movement of the pipetting arm.

5. The bottom sensing device of claim 1, wherein the mounting means is a spring mechanism.

6. The bottom sensing device of claim 5, wherein the spring mechanism is provided about a tip of the pipetting probe proximate to the pipetting arm.

7. The bottom sensing device of claim 6, wherein the spring mechanism permits the pipetting arm to move independent of the pipetting probe.

8. A method of determining a bottom of a container, comprising:

lowering a pipetting arm having a pipetting tip to the bottom of the container;

incrementally lowering the pipetting arm a predetermined distance, while the pipetting tip remains in contact with the bottom of the container;

triggering a sensor when the pipetting arm has been incrementally lowered a certain distance; determining the bottom of the container when the sensor is triggered.

9. The method of claim 8, further comprising stopping the incrementally lowering of the pipetting arm when the when the sensor is triggered.

10. The method of claim 8, further comprising incrementally raising the pipetting arm when the sensor is triggered in order to eliminate obstructions of the pipetting tip when aspirating the fluid.

11. The method of claim 8, further comprising determining a top level of a fluid in relation to a home position prior to the pipetting tip contacting the bottom of the container.

12. The method of claim 11, further comprising determining a volume of the fluid in the container, the volume being based on (i) a known shape of a type of container used to hold a sample fluid, (ii) the top level of the fluid and (iii) a distance from the top level of the fluid to the bottom of the container.

* * * * *